US009302007B2

(12) United States Patent
Henderson

(10) Patent No.: US 9,302,007 B2
(45) Date of Patent: Apr. 5, 2016

(54) LOW SURFACTANT IODINE TOPICAL DISINFECTANT

(75) Inventor: Mark Henderson, Basehor, KS (US)

(73) Assignee: DELAVAL HOLDING AB, Tumba (SE)

( * ) Notice: Subject to any disclaimer, the term of this patent is extended or adjusted under 35 U.S.C. 154(b) by 35 days.

(21) Appl. No.: 14/005,725

(22) PCT Filed: Mar. 23, 2012

(86) PCT No.: PCT/US2012/030417

§ 371 (c)(1), (2), (4) Date: Sep. 17, 2013

(87) PCT Pub. No.: WO2012/135055

PCT Pub. Date: Oct. 4, 2012

(65) Prior Publication Data

US 2014/0010881 A1 Jan. 9, 2014

Related U.S. Application Data

(60) Provisional application No. 61/467,874, filed on Mar. 25, 2011.

(51) Int. Cl.

*A61K 47/00* (2006.01)
*A61K 47/10* (2006.01)
*A01N 59/12* (2006.01)
*A61K 33/18* (2006.01)

(52) U.S. Cl.

CPC ................ *A61K 47/10* (2013.01); *A01N 59/12* (2013.01); *A61K 33/18* (2013.01)

(58) Field of Classification Search

None

See application file for complete search history.

(56) References Cited

U.S. PATENT DOCUMENTS

| | | | | |
|---|---|---|---|---|
| 3,728,449 | A * | 4/1973 | Cantor et al. | 424/671 |
| 4,125,602 | A * | 11/1978 | Atasoy et al. | 525/358 |
| 4,271,149 | A | 6/1981 | Winicov et al. | |
| 5,302,392 | A * | 4/1994 | Karakelle et al. | 424/409 |
| 5,616,348 | A * | 4/1997 | Winicov | 424/667 |
| 5,643,608 | A * | 7/1997 | McKinzie et al. | 424/667 |
| 5,885,620 | A * | 3/1999 | Foret | 424/669 |
| 6,107,344 | A | 8/2000 | Loosemore | |
| 6,153,229 | A | 11/2000 | Foret | |
| 6,379,685 | B1 * | 4/2002 | Richter et al. | 424/405 |
| 6,395,289 | B1 * | 5/2002 | Ehrhard et al. | 424/407 |
| 6,586,477 | B1 * | 7/2003 | Schattner | 514/731 |
| 7,845,351 | B2 * | 12/2010 | Mathis et al. | 128/206.21 |
| 2001/0036482 | A1 * | 11/2001 | Fredell et al. | 424/667 |
| 2003/0235560 | A1 * | 12/2003 | Harrison | 424/93.6 |
| 2004/0091553 | A1 | 5/2004 | Foret | |
| 2005/0031705 | A1 | 2/2005 | Tyndall et al. | |
| 2009/0004122 | A1 * | 1/2009 | Modak et al. | 424/49 |
| 2013/0121953 | A1 * | 5/2013 | Lentini | 424/78.07 |

FOREIGN PATENT DOCUMENTS

| | | |
|---|---|---|
| WO | 9616546 | 6/1996 |
| WO | 02/23993 | 3/2002 |
| WO | 2005/048709 | 6/2005 |

OTHER PUBLICATIONS

International Search Report and Written Opinion dated Oct. 25, 2012 in the corresponding PCT/US2012/030417 application filed Mar. 23, 2012.

Extended European Report dated Oct. 10, 2014, from the EP 12765400.2 filed on Oct. 22, 2013.

* cited by examiner

*Primary Examiner* — Robert A. Wax
*Assistant Examiner* — Olga V Tcherkasskaya
(74) *Attorney, Agent, or Firm* — Hovey Williams LLP

(57) ABSTRACT

Iodine-containing germicidal compositions are disclosed that remain physically stable for extended storage periods with little to no iodine complexing agent being present. The compositions employ a mixture of emollients, such as glycerin and ethoxylanolin, to create a composition that in certain embodiments presents a cloudy or emulsion-like appearance.

23 Claims, 2 Drawing Sheets

LOW SURFACTANT IODINE TOPICAL DISINFECTANT

RELATED APPLICATION

The present application claims the benefit of U.S. Provisional Patent Application No. 61/467,874, filed Mar. 25, 2011, which is incorporated by reference herein in its entirety.

BACKGROUND OF THE INVENTION

1. Field of the Invention

The present invention is directed toward an iodine topical disinfectant dip which provides reduced irritation and enhanced moisturizing effect to the skin as compared with other conventional topical disinfectants. Such topical disinfectants include hand sanitizers, surgical scrubs, surgical solutions and dairy cow teat disinfectants. Teat dips according to the present invention are particularly useful in extremely dry and/or windy conditions.

2. Description of the Prior Art

Iodine solutions have been used as germicidal agents for many years, and especially in the formation of teat dip products for the prevention of mastitis in cows. In order to create useful solutions of this type, it is necessary to solubilize the iodine therein. Different solubilization approaches have been used in the past, some of which are discussed in greater detail below. Other approaches have involved the use of surfactants or polymers such as PVP that complex with iodine and yield solutions (generally referred to as iodophores). Some prior iodine-containing compositions can be quite irritating to animal skin, particularly when used under particular weather-related conditions. Thus, it is incumbent to utilize a teat dip that avoids skin irritation as better teat skin condition means less chance of harboring mastitis-causing pathogens and presumably more comfort for the cow.

U.S. Pat. No. 5,885,620 is directed toward stable aqueous glycerin iodine concentrates that are adapted for dilution in water to yield germicidal iodine use solutions. The concentrates include from about 30-87% by weight glycerin, from about 0.15-15% by weight iodine, from about 0.15-15% by weight iodide ion, and one or more additives such as compatible wetting agents, hydrotropes, thickening agents, additional emollients and buffering systems.

U.S. Pat. No. 6,153,229 is directed toward stable aqueous glycerin iodine concentrates that are adapted for dilution in water to yield germicidal iodine use solutions. The concentrates include glycerin, iodine, and iodide ion. The quantities of iodide ion and iodine are such that the ratio of iodide ion to iodine is from about 0.5:1 to about 6:1.

U.S. Pat. No. 5,643,608 is directed toward stable aqueous iodine/iodide/iodate germicidal compositions that have relatively high quantities of free iodine therein and also substantially maintain the starting amounts of available and free iodine throughout a storage period of at least about three months. These compositions contain from about 0.01-1.4% by weight available iodine, from about 10-125 ppm free iodine, from about 0.005-0.5% by weight iodate ion, from about 0.1-15% by weight of iodine complexing agent, from about 0.004-0.5% by weight iodide ion, and have a pH of from about 2.0-4.5.

U.S. Patent Application Publication No. 2004/0091553 is directed toward aqueous, ready-to-use iodine teat dip compositions that are specially formulated for winter time use to permit application to cows teats without freezing. The compositions include from about 0.01-2% by weight iodine, from about 0.01-3% by weight iodide ion, and from about 35-75% by weight of an additive such as glycerin. The compositions have free iodine values of from about 1-60 ppm at 25° C. and from about 0.5-20 ppm at 4° C.

SUMMARY OF THE INVENTION

In certain embodiments according to the present invention, there is provided an aqueous germicidal composition comprising iodine as the germicidal agent and little to no iodine complexing agent.

In other embodiments according to the present invention, there is provided an aqueous germicidal composition comprising iodine as the germicidal agent and at least two separate emollients. In particular embodiments, one emollient is present in an amount greater than the other emollient. In still other embodiments, the principal emollient is selected from the group consisting of glycerin, propylene glycol, sorbitol, polyethylene glycol or mixtures thereof, and the secondary emollient is a water-dispersible lanolin derivative, such as ethoxylanolin.

In yet other embodiments according to the present invention, there is provided an aqueous, iodine-containing, germicidal composition comprising little to no surfactant or polymer iodine complexing agent. In these embodiments, a combination of emollients, particularly glycerin and ethoxylanolin are used to solubilize or stably disperse the iodine and provide a composition having a cloudy or hazy appearance. In certain embodiments, iodide can also be used to assist with solubilizing iodine.

In still other embodiments according to the present invention, there is provided a ready-to-use germicidal composition comprising less than 0.5% by weight of a surfactant or polymer iodine complexing agent. The composition generally comprises from about 0.05 to about 1.5% by weight of iodine, from 0.05 to about 10% by weight of water-soluble lanolin derivative, and at least one gum thickener. As a ready-to-use formulation, the composition may be applied to an animal's teat without further dilution.

In still other embodiments according to the present invention, there is provided methods for treating animal skin, particularly bovine teats, by applying thereto a germicidal composition as described herein.

DETAILED DESCRIPTION OF THE PREFERRED EMBODIMENT

Figure 1:
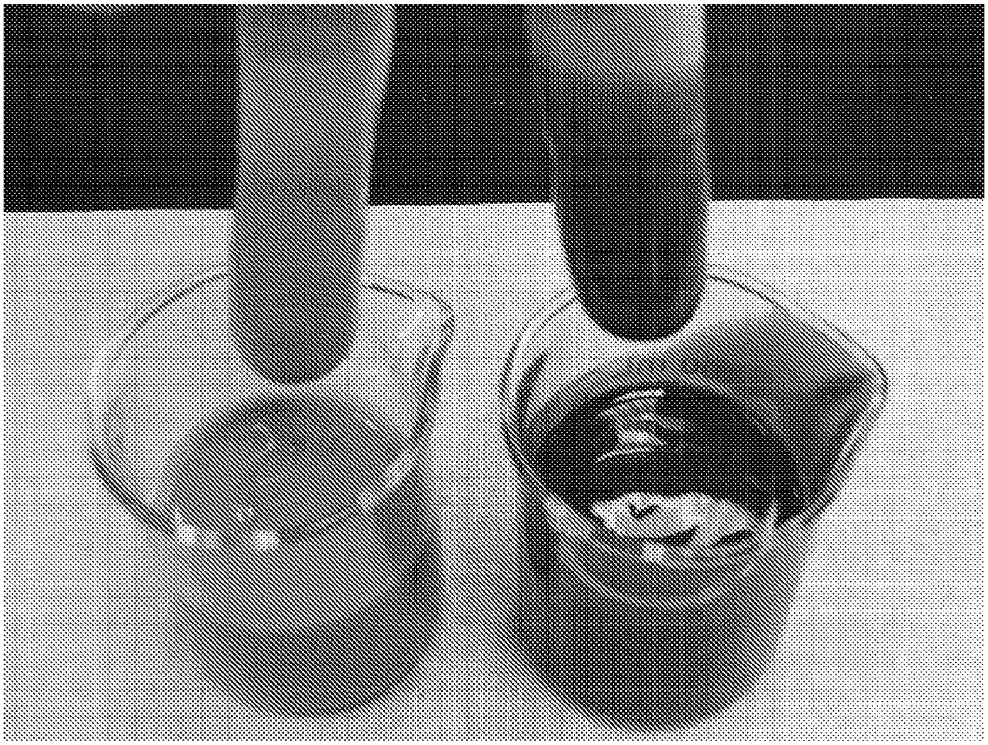
FIG. 1 is a photograph comparing the appearance on skin of a commercially available teat dip composition and an exemplary composition made in accordance with the present invention.

The present invention is generally directed toward teat dip compositions that comprise germicidally effective amounts of iodine that remains physically stable within the composition without the use of or using only very small amounts of iodine complexing agents, especially surfactant or polymer iodine complexing agents. Iodine itself is not soluble in water to any appreciable extent (only about 300 ppm at room temperature). In order to create aqueous iodine-containing compositions a solvent for the iodine, such as an alcohol, or an iodine complexing agent, such as iodide ion or a surfactant, must be used. Alcohols, such as isopropyl alcohol, and traditional iodine complexing agents can cause irritation to animal skin, particularly when used in relatively large amounts.

The present invention overcomes these shortcomings of traditional iodine-based germicidal compositions by employing a combination of skin-friendly emollients in which the iodine is dispersed with minimal to no traditional iodine complexing agents. Thus, the resulting composition is less irritating to animal skin, but remains physically stable for extended storage periods.

In certain embodiments according to the present invention, the germicidal composition is a ready-to-use aqueous formulation that does not require further dilution prior to application to the animal. In particular embodiments, the composition comprises at least two emollient components. The first, or primary, emollient may comprise glycerin, propylene glycol, sorbitol, polyethylene glycol, or mixtures thereof. Particularly, the primary emollient is present in the composition at a level of between about 5 to about 75% by weight, between about 10 to about 50% by weight, or between about 20 to about 30% by weight, based upon the weight of the entire composition.

The secondary emollient is generally present in lesser amounts than the primary emollient, but this need not always be the case. In certain embodiments according to the present invention, the secondary emollient is a water-dispersible, or even water-soluble, lanolin derivative, such as an alkoxylated lanolin composition (e.g., ethoxylanolin). An exemplary ethoxylanolin composition is a PEG-75 lanolin composition available under the name Laneto 50 from RITA Corporation. Further exemplary water-dispersible lanolin derivatives include acetylated lanolin, hydroxylated lanolin, lanolin alcohols and lanolin acids. Lanolin alcohols and acid can further be acetylated, hydroxylated, and alkoxylated. This secondary emollient can be used at a level of between about 0.05 to about 10% by weight, between about 0.1 to about 5% by weight, or between about 0.5 to about 3% by weight, based upon the weight of the entire composition.

Certain embodiments of the present invention contain iodine present at a level of between about 0.05% to about 1.5% by weight, or between about 0.2 to about 0.9% by weight, or between 0.25 to about 0.75% by weight based on the total weight of the composition. It is noted that the foregoing iodine amounts are traditionally referred to as the "available iodine" in the composition. This is contrasted with the "free iodine" in the composition. As used herein, "free iodine" is the concentration of $I_2$ which is not complexed with other species such as iodide ions $I_3^-$ or other complexing agents. A certain concentration of free iodine $I_2$ is always present in iodine solutions because of equilibrium reactions such as $I_3^- \leftrightarrows I_2 + I^-$, or in general, $I_2$ (complexing agent)$\leftrightarrows I_2+$ complexing agent. Free iodine is preferably determined by the method of Winicov et al., Proc. Int. Symposium on Povidone, University of Kentucky College of Pharmacy, pp. 186-92 (1983), incorporated by reference herein. In certain embodiments, the compositions have a free iodine concentration of between about 1 to about 25 ppm, between about 2 to about 15 ppm, between about 3 to about 10 ppm, or about 5 ppm.

In order to make incorporation of iodine into the teat dip compositions of the present invention more convenient, the iodine may be provided initially in the form of a concentrated glycerin dispersion. In order to ensure the chemical stability of the iodine in this concentrated dispersion, the dispersion also comprises minor levels of iodide ion. One exemplary iodine/glycerin concentrate is formulated as follows: 28.5% by weight iodine, 12.3% by weight sodium iodide, 48% by weight glycerin, and 11.2% by weight water. However, it is within the scope of the present invention for iodine to be directly added into the composition without having first been dispersed in an intermediate.

It has been discovered that at certain iodine to secondary emollient ratios, that the compositions acquires a velvety, hazy, or milky appearance that resembles a suspension or an emulsion. This characteristic imparts a smooth feel or texture to the teat dip composition. In addition, this feature causes the composition as a whole to take on an opaque appearance, which further accentuates the relatively low iodine levels present in the composition. Thus, it becomes much easier to visually identify the composition on the animal's skin once applied. In certain embodiments, the ratio of iodine to secondary emollient is between about 1:0.01 to about 1:25, about 1:0.05 to about 1:25, about 1:0.025 to about 1:25, about 1:0.1 to about 1:25, about 1:1 to about 1:20, or between about 1:2 to about 1:12, or between about 1:3 to about 1:8. In certain embodiments the velvety, hazy, or milky appearance can be attributed to particles suspended in the composition. In particular embodiments, it has been discovered that the particles form in the presence of iodine and have an average particle size of between about 25 nm to about 5 μm, between about 75 nm to about 2.5 μm, between about 100 nm to about 1 μm, or between about 250 nm to about 750 nm, as determined by photomicroscopy (a Nikon light microscope at 400× magnification was employed). Particle size was also confirmed by dynamic light scattering (DLS) using a Zetasizer instrument. In DLS testing, samples were diluted with water in order to obtain a workable particle concentration for the instrument. DLS testing was performed at 25° C. over an 80 second duration. The count rate was 140.3 kcps, the measurement position was 0.65 mm, and the attenuator setting was 3. It is believed that the particles comprise iodine that is complexed with at least some of the secondary emollient, such as a lanolin derivative.

Figure 2:
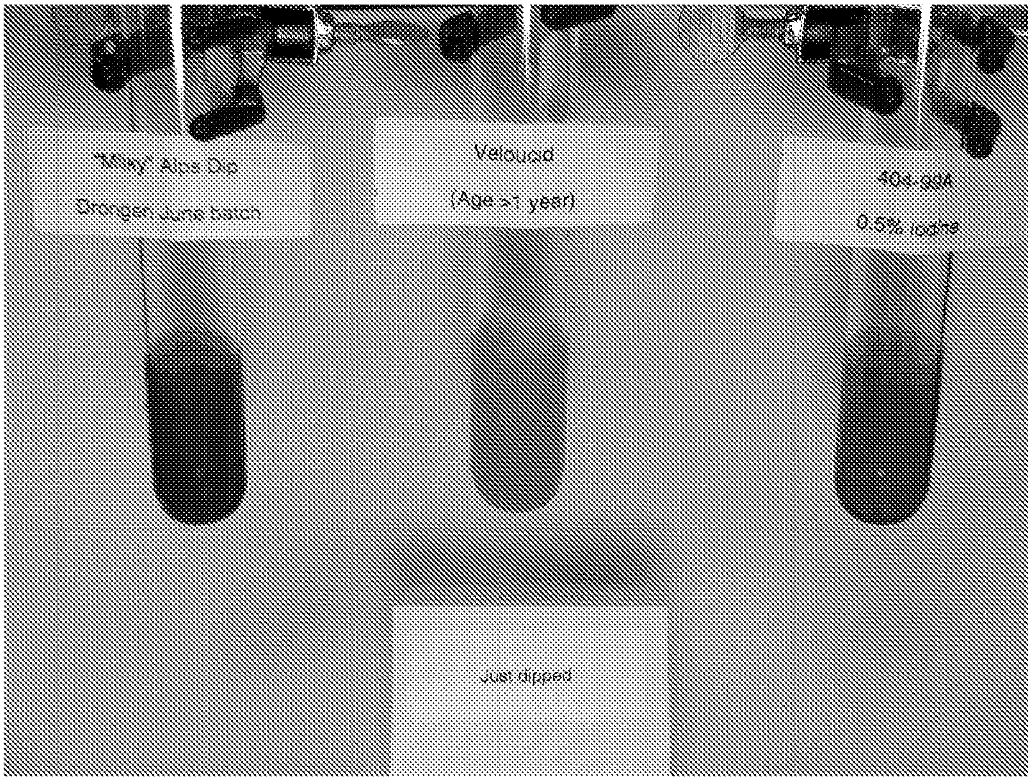
FIG. 2 is a photograph comparing the appearance of a teat dip composition made in accordance with the present invention, a commercially available teat dip composition, and an iodine solution.

These aesthetic aspects are illustrated in FIGS. 1 and 2. In FIG. 1, the composition on the left is a commercial composition, VELOUCID, a film-forming emulsion based on iodine complexed with PVP available from Ecolab. The composition on the right is an exemplary composition according to the present invention, particularly formulation 6 of Table 1 below. It can be seen that formulation 6 is darker in color, but exhibits a very similar milky/hazy appearance that shows up well when applied to skin. In FIG. 2, formulation 6 was dipped onto the far left test tube, VELOUCID onto the center test tube, and a 0.5% iodine solution onto the far right test tube. The 0.5% iodine solution is much clearer in appearance and does not exhibit the milky/hazy appearance of formulation 6 and VELOUCID. Thus, the present invention is able to achieve very similar aesthetic characteristics of the VELOUCID composition, without the use of a traditional iodine-surfactant complex.

As noted above, the use of traditional complexing agents can be avoided or substantially reduced. Particularly, embodiments according to the present invention present an iodide/iodine ratio of between about 0 (no iodide) to about 0.6:1, between about 0.001 to about 0.5, between about 0.005:1 to about 0.25:1, or between about 0.01:1 to about 0.1:1. Although not added for purposes of complexing iodine, iodide ion and iodate ion can be added to the composition to provide for chemical stability of the iodine thereby ensuring levels of available iodine are maintained according to the following chemical equation:

$$IO_3^- + 5I^- + 6H^+ \rightarrow 3I_2 + 3H_2O$$

Compositions according to the present invention may comprise iodide ion, added to the composition as sodium or potassium iodide, at a level of between 0 to about 1% by weight, or between about 0.001 to about 0.5% by weight, or between about 0.01 to about 0.25% by weight.

Also, certain embodiments according to the present invention comprise little or no surfactant which is capable of complexing with iodine. Exemplary iodine-complexing surfactants or polymers that can be excluded from the present inventive compositions, or used very sparingly, include nonylphenol ethoxylate, alcohol ethoxylate, alcohol alkoxylate, ethylene oxide-propylene oxide copolymers (such as Pluronic surfactants available from BASF), and PVP. Accordingly, such iodine-complexing surfactants are present in the compositions at a level of less than 1.5% by weight, less than 0.5% by weight, less than 0.1% by weight. In other embodiments according to the present invention the ratio of iodine to iodine complexing surfactant or polymer is 1:<2, or 1:<1, or 1:<0.5.

Compositions in accordance with certain embodiments of the present invention should be stable for a period of at least one month at room temperature (i.e., about 25° C.) storage, preferably for a period of three months, more preferably for a period of at least about six months, and most preferably for a period of at least about one year. As used herein with reference to the compositions "stable" means that the compositions remain as substantially homogeneous solutions or suspensions, with little to no visible iodine precipitation and no substantial layering or separation, throughout a given storage period at room temperature and at least 80%, and in some embodiments, at least 90% of the starting iodine concentration remains.

The pH of the composition is adjusted so as to be within a desired range. Buffer compositions may be employed to help maintain the pH within this desired range. Exemplary buffers include citric acid and sodium hydroxide. In certain embodiments, the pH of the composition is between about 3 to about 6, or between about 3.5 to about 5.5, or between about 4 to about 5.5.

In certain embodiments, a non-iodine complexing wetting agent can be used to help improve the feel of the composition or to improve wetting properties. Exemplary wetting agents include AEROSOL OT 75, sodium dioctyl sulfosuccinate, available from Cytec Industries, West Paterson, N.J. Other exemplary wetting agents include sulfonates such as the alkyl sulfonates, aryl sulfonates, alkyl aryl sulfonates, alkyl diphenyloxide disulfonate, dialkyl sodium sulfosuccinates, sulfonated amphoterics such as alkylamphohydroxy propyl sulfonate, polysulfonates such as lignosulfate, $C_8$-$C_{16}$ alkyl polyglycosides, sodium alcohol sulfates, and mixtures thereof. The wetting agent should be present at levels that do not exceed 2% by weight, or 0.25% by weight, or 0.1% by weight.

Compositions according to the present invention may also comprise thickeners to adjust the viscosity of the composition. Exemplary thickeners include cellulose derivatives such as hydroxy ethylcellulose and carboxy methylcellulose, sodium alginate, xanthan gum, gum arabic, carageenan and mixtures thereof. The thickeners can be used at a level of between 0 to about 5% by weight, or between about 0.01 to about 2% by weight, or between about 0.05 to about 1% by weight and are used to create approximate viscosities of 2 to 5000, to 4000, 30 to 3000, 100 to 2500, 250 to 2000, 400 to 1500, 500 to 1250, or 700 to 1000 cP. The viscosities disclosed herein, unless otherwise indicated, were measured using a Brookfield LV viscometer using spindle #2 at 12 rpm, in the range of about 2000 cP and below, and 6 rpm for viscosities greater than about 2000 cP.

EXAMPLES

Table 1 provides several exemplary formulations made in accordance with the present invention. It is understood, however, that these examples are provided by way of illustration and nothing therein should be taken as a limitation upon the overall scope of the invention.

TABLE 1

| Ingredients (% w/w) | 1 | 2 | 3 | 4 | 5 | 6 | 7 | 8 | 9 |
|---|---|---|---|---|---|---|---|---|---|
| Pluronic P105 | — | 0.25 | 0.20 | 0.30 | — | — | — | — | — |
| Glycerin | 24.50 | 24.50 | 24.50 | 24.50 | 24.10 | 24.50 | 24.50 | 24.50 | 24.50 |
| Laneto 50 (PEG-75 lanolin) | 1.00 | 1.00 | 1.00 | 1.00 | 1.50 | 1.50 | 1.30 | 1.50 | 1.70 |
| Citric Acid monohydrate | 0.10 | 0.10 | 0.10 | 0.10 | 0.10 | 0.10 | 0.10 | 0.10 | 0.10 |
| Xanthan Gum (Keltrol) | 0.35 | 0.40 | 0.45 | 0.45 | 0.50 | 0.50 | 0.50 | 0.50 | 0.50 |
| Sodium iodide, 57% | 0.40 | — | — | — | — | — | — | — | — |
| Glycerin-iodine concentrate* | 0.95 | 0.90 | 0.90 | 0.90 | 0.80 | 0.90 | 0.90 | 0.90 | 0.90 |
| Sodium iodate | — | 0.10 | 0.15 | 0.15 | 0.10 | 0.10 | 0.10 | 0.10 | 0.10 |
| Aerosol OT 75 | — | 0.05 | 0.05 | 0.05 | 0.05 | 0.05 | 0.05 | 0.05 | 0.05 |
| NaOH 50% (10%) | 0.05 | 0.08 | 0.08 | 0.08 | 0.12 | 0.14 | (0.50) | (0.50) | (0.50) |
| Water | 72.65 | 72.62 | 72.57 | 72.47 | 72.73 | 72.21 | 72.05 | 71.85 | 71.80 |
| pH target | 4 | 5.5 | 5.5 | 5.5 | 4 | 5 | 5.5 | 5.5 | 5.5 |

*Glycerin-iodine concentrate comprising 28% iodine.

Formulations 1-9 all exhibited a hazy appearance, and exhibited shelf stability for at least one month. Further, formulas 7-8 suggesting that varying the ethoxylanolin concentration from 1.3 wt. % to 1.7 wt. % does not affect stability.

Tables 2-16 provide several additional exemplary formulations made in accordance with the present invention. The glycerin-iodine complex utilized in the formulations of Tables 2-15 comprised 0.36 g of iodide and 1.7 g of glycerin for every gram of iodine ($I_2$). All of the above compositions show acceptable stability and provide and hazy appearance.

TABLE 2

Variations on Iodine/Lanolin ratios

| Ingredients (% w/w) | Formulations D | E | F | G | H | I | J | K | L |
|---|---|---|---|---|---|---|---|---|---|
| Laneto 50 | 0.20 | 0.20 | 0.20 | 1.50 | 1.50 | 1.50 | 10.00 | 10.00 | 10.00 |
| Glycerin | 0.00 | 25.00 | 50.00 | 0.00 | 25.00 | 50.00 | 0.00 | 25.00 | 50.00 |
| Glycerin-iodine complex | 0.90 | 0.90 | 0.90 | 0.90 | 0.90 | 0.90 | 0.90 | 0.90 | 0.90 |
| DI Water | 98.90 | 73.90 | 48.90 | 97.60 | 72.60 | 47.60 | 89.10 | 64.10 | 39.10 |
| Amount of undissolved iodine | 1 | 1 | 1 | 1 | 1 | 1 | 3 | 3 | 3 |
| % avail iodine | 0.25 | 0.25 | 0.25 | 0.25 | 0.25 | 0.25 | 0.25 | 0.25 | 0.25 |
| % ethoxylanolin | 0.10 | 0.10 | 0.10 | 0.75 | 0.75 | 0.75 | 5.00 | 5.00 | 5.00 |
| iodine/lanolin ratio | 2.5 | 2.5 | 2.5 | 0.3 | 0.3 | 0.3 | 0.1 | 0.1 | 0.1 |

| Ingredients (% w/w) | Formulations M | N | O | P | Q | R | S | T | U |
|---|---|---|---|---|---|---|---|---|---|
| Laneto 50 | 0.20 | 0.20 | 0.20 | 1.50 | 1.50 | 1.50 | 10.00 | 10.00 | 10.00 |
| Glycerin | 0.00 | 25.00 | 50.00 | 0.00 | 25.00 | 50.00 | 0.00 | 25.00 | 50.00 |
| Glycerin-iodine complex | 1.8 | 1.8 | 1.8 | 1.8 | 1.8 | 1.8 | 1.8 | 1.8 | 1.8 |
| DI Water | 98.00 | 73.00 | 48.00 | 96.70 | 71.70 | 46.70 | 88.20 | 63.20 | 38.20 |
| Amount of undissolved iodine | 2 | 1 | 1 | 1 | 2 | 2 | 3 | 3 | 3 |
| % avail iodine | 0.5 | 0.5 | 0.5 | 0.5 | 0.5 | 0.5 | 0.5 | 0.5 | 0.5 |
| % ethoxylanolin | 0.10 | 0.10 | 0.10 | 0.75 | 0.75 | 0.75 | 5.00 | 5.00 | 5.00 |
| iodine/lanolin ratio | 5.0 | 5.0 | 5.0 | 0.7 | 0.7 | 0.7 | 0.1 | 0.1 | 0.1 |

| Ingredients (% w/w) | Formulations V | W | X | Y | Z | AA | BB | CC | DD |
|---|---|---|---|---|---|---|---|---|---|
| Laneto 50 | 0.20 | 0.20 | 0.20 | 1.50 | 1.50 | 1.50 | 10.00 | 10.00 | 10.00 |
| Glycerin | 0.00 | 25.00 | 50.00 | 0.00 | 25.00 | 50.00 | 0.00 | 25.00 | 50.00 |
| Glycerin-iodine complex | 3.6 | 3.6 | 3.6 | 3.6 | 3.6 | 3.6 | 3.6 | 3.6 | 3.6 |
| DI Water | 96.20 | 71.20 | 46.20 | 94.90 | 69.90 | 44.90 | 86.40 | 61.40 | 36.40 |
| Amount of undissolved iodine | 3 | 3 | 1 | 2 | 2 | 3 | 3 | 3 | 3 |
| % avail iodine | 1 | 1 | 1 | 1 | 1 | 1 | 1 | 1 | 1 |
| % ethoxylanolin | 0.10 | 0.10 | 0.10 | 0.75 | 0.75 | 0.75 | 5.00 | 5.00 | 5.00 |
| iodine/lanolin ratio | 10.0 | 10.0 | 10.0 | 1.3 | 1.3 | 1.3 | 0.2 | 0.2 | 0.2 |

Amount of undissolved Iodine:
0 = none;
1 = trace;
2 = moderate;
3 major amount

The formulations in Table 2 were prepared and observed for the presence of residue (iodine crystals) after mixing. All formulations had an emulsion-like appearance, with the exception of formulations J, K, and L, which appeared clear. Further, all formulations were unable to dissolve all the iodine, as evidenced by the presence of residue. These examples do not contain and adequate amount of thickener.

TABLE 3

Effect of a Thickener on Iodine Solubility

| | Formulations (% w/w) 35A | 35B |
|---|---|---|
| Laneto 50 | 1.5 | 1.5 |
| Glycerin | 25 | 25 |
| Glycerin-iodine complex | 0.9 | 0.9 |
| DI Water | 72.6 | 72.6 |
| Xanthan gum | 0 | 0.1 |
| Undissolved Iodine present? | Fair amount | Very minor trace amount |

The results of Table 3 suggested that the presence of a thickener (or increased viscosity, in general) can decrease the amount of undissolved iodine present after mixing.

Tables 4a and 4b: Variation of Xanthan Gum Concentrations and Effect of Iodine Solubility TABLE 4a

| | Formulations A | B | C | D |
|---|---|---|---|---|
| Ingredients (% w/w) | | | | |
| 0.3% xanthan gum stock | 3.3 | 16.7 | 33.4 | 50.1 |
| Laneto 50 | 1.5 | 1.5 | 1.5 | 1.5 |
| Glycerin | 25.0 | 25.0 | 25.0 | 25.0 |
| Glycerin-iodine complex | 0.9 | 0.9 | 0.9 | 0.9 |
| DI Water | 69.3 | 55.9 | 39.2 | 22.5 |
| % xanthan gum (Keltrol RD) | 0.01 | 0.05 | 0.10 | 0.15 |
| Iodine crystals on top? | yes | yes, less than A* | yes, less than A* | no |
| Viscosity, 23 C., sp. 2, cP | | | | |
| 30 rpm | | — | 65 | 131 |
| 60 rpm | | — | 46 | 85 |

*Formulations B&C had about the same amount of crystals

TABLE 4b

| | Formulations | | |
|---|---|---|---|
| | A | B | C |
| **Ingredients (% w/w)** | | | |
| 0.5% xanthan gum stock | 30.0 | 40.0 | 50.0 |
| Laneto 50 | 1.5 | 1.5 | 1.5 |
| Glycerin | 25.0 | 25.0 | 25.0 |
| Glycerin-iodine complex | 0.9 | 0.9 | 0.9 |
| DI Water | 42.6 | 32.6 | 22.6 |
| % xanthan gum (Keltrol RD) | 0.15 | 0.20 | 0.25 |
| iodine crystals on top? | No | no | no |
| Residue on bottom at 2 wks? | yes | no | no |
| **Viscosity, 22 C., sp. 1, cP** | | | |
| 6 rpm | — | — | 943 |
| 12 rpm | — | 392 | — |
| 30 rpm | 135 | — | |
| 60 rpm | 88 | — | — |
| Viscosity, 22 C., sp. 2, 20 rpm | 167 | 280 | 414 |

All formulations prepared in Tables 4a and 4b had an emulsion like appearance after mixing. These results suggested that a minimum amount of xanthan gum in the range of 0.1 to 0.15% provided initial homogeneity. Further, the results suggested that a minimum amount of xanthan gum in the range of 0.15 to 0.2% provided for two week homogeneity.

Tables 5a, 5b, and 5c: Effect of Various Thickeners

TABLE 5a

Thickener Legend for Tables 5b and 5c

| Formulation reference | Stock Solution (% w/w) | Thickener | Type |
|---|---|---|---|
| A | 0.5 | Natrosol 250HR (AF030) | Hydroxyethylcellulose (DP* = 3700) |
| B | 0.5 | Natrosol 250KR (AF041) | Hydroxyethylcellulose (DP* = 2000) |
| C | 1 | TIC Ticalose CMC15 | Carboxymethylcellulose (low polymerization) |
| D | 0.5 | TIC Ticalose CMC6000 | Carboxymethylcellulose (medium polymerization) |
| E | 0.375 | TIC Ticalose CMC15000 | Carboxymethylcellulose (high polymerization) |
| F | 0.5 | TIC TICA-algin HG600F | Sodium alginate |
| G | 1 | TIC Colloid PM-9399 | Carageenan + NaCl |

*DP = degree of polymerization

TABLE 5b

| | Formulations | | | | | | |
|---|---|---|---|---|---|---|---|
| Ingredients (% w/w) | A1 | B1 | C1 | D1 | E1 | F1 | G1 |
| Thickener stock solution | 30.00 | 30.00 | 15.00 | 30.00 | 40.00 | 30.00 | 15.00 |
| Laneto 50 | 1.50 | 1.50 | 1.50 | 1.50 | 1.50 | 1.50 | 1.50 |
| Glycerin | 25.00 | 25.00 | 25.00 | 25.00 | 25.00 | 25.00 | 25.00 |
| Glycerin-iodine complex | 0.90 | 0.90 | 0.90 | 0.90 | 0.90 | 0.90 | 0.90 |
| DI Water | 42.60 | 42.60 | 57.60 | 42.60 | 32.60 | 42.60 | 57.60 |
| Viscosity, sp 1, 60 rpm | 12.0 | 9.3 | 7.6 | 41.0 | 55.0 | 13.7 | 8.7 |
| % thickener | 0.15 | 0.15 | 0.15 | 0.15 | 0.15 | 0.15 | 0.15 |
| iodine crystals on top initially? | no | yes | yes | yes | yes | yes | yes |
| iodine crystals on bottom after 1 day? | mod | mod | mod | heavier | light | mod | light |

TABLE 5c

| | Formulations | | | | | | | | |
|---|---|---|---|---|---|---|---|---|---|
| Ingredients (% w/w) | A2 | B2 | C2 | D2 | E2 | F2 | G2 | D3 | G3 |
| Thickener stock solution | 72.6 | 72.6 | 72.6 | 72.6 | 72.6 | 72.6 | 72.6 | 74.1 | 74.1 |
| Laneto 50 | 1.5 | 1.5 | 1.5 | 1.5 | 1.5 | 1.5 | 1.5 | none | none |
| Glycerin | 25.0 | 25.0 | 25.0 | 25.0 | 25.0 | 25.0 | 25.0 | 25.0 | 25.0 |
| Glycerin-iodine complex | 0.9 | 0.9 | 0.9 | 0.9 | 0.9 | 0.9 | 0.9 | 0.9 | 0.9 |
| DI Water | 0.0 | 0.0 | 0.0 | 0.0 | 0.0 | 0.0 | 0.0 | — | — |
| Viscosity, sp 1, 60 rpm | 53.0 | 21.0 | 15.0 | >100 | >100 | 42.0 | 64.0 | — | — |
| Viscosity, sp 1, 12 rpm | — | — | — | 244.0 | — | — | — | — | — |
| Viscosity, sp 1, 30 rpm | — | — | — | — | 191.0 | — | — | — | — |
| % thickener | 0.36 | 0.36 | 0.73 | 0.36 | 0.27 | 0.36 | 0.73 | 0.37 | 0.74 |
| iodine crystals on top initially? | no | no | yes | very slt | yes | yes | no | Clear, homo geneous | 2 layers Top-clear Bottom-opaque |
| iodine crystals on bottom initially? | yes | yes | yes | yes | no | no | no | | |
| iodine crystals on bottom after 3 days? | NA | NA | NA | heavy | NA | NA | slt on top, none on bottom | | |

In the above tables, the effect of thickeners besides xanthan gum was evaluated. All formulations from Tables 5b and 5c had an emulsion-like appearance however, most of the formulations contained iodine crystals. Furthermore, most of the formulations from Tables 5b and 5c had a lower viscosity than the formulations from Tables 4a and 4b, which contained xanthan gum as a thickener.

Tables 6a and 6b

TABLE 6a

Stock Solutions for use in Formulations of Table 6b

| Ingredients (g) | Stock Solutions | | | | | | | | |
|---|---|---|---|---|---|---|---|---|---|
| | A1 | A2 | A3 | B1 | B2 | B3 | C1 | C2 | C3 |
| Laneto 50 (50% active) | 0.2 | 0.2 | 0.2 | 1.5 | 1.5 | 1.5 | 10.0 | 10.0 | 10.0 |
| Glycerin | 0.0 | 25.0 | 50.0 | 0.0 | 25.0 | 50.0 | 0.0 | 25.0 | 50.0 |
| 0.55% Xanthan gum in DI water | 36.4 | 36.4 | 36.4 | 36.4 | 36.4 | 36.4 | 36.4 | 36.4 | 36.4 |
| DI water | 59.8 | 34.8 | 9.8 | 58.5 | 33.5 | 8.5 | 50.0 | 25.0 | 0.0 |

TABLE 6b

| Ingredients (% w/w) | Formulations | | | | | | | | |
|---|---|---|---|---|---|---|---|---|---|
| | D | E | F | G | H | I | J | K | L |
| Stock soln reference | A1 | A2 | A3 | B1 | B2 | B3 | C1 | C2 | C3 |
| Stock soln | 96.4 | 96.4 | 96.4 | 96.4 | 96.4 | 96.4 | 96.4 | 96.4 | 96.4 |
| Glycerin-iodine complex | 0.9 | 0.9 | 0.9 | 0.9 | 0.9 | 0.9 | 0.9 | 0.9 | 0.9 |
| DI Water | 2.7 | 2.7 | 2.7 | 2.7 | 2.7 | 2.7 | 2.7 | 2.7 | 2.7 |
| Laneto 50 (from stock) | 0.2 | 0.2 | 0.2 | 1.5 | 1.5 | 1.5 | 10.0 | 10.0 | 10.0 |
| Glycerin (from stock) | 0.0 | 25.0 | 50.0 | 0.0 | 25.0 | 50.0 | 0.0 | 25.0 | 50.0 |
| Amount of undissolved iodine* | 0 | 0 | 0 | 0 | 0 | 0 | 2 | 1 | 0 |
| % avail iodine | 0.25 | 0.25 | 0.25 | 0.25 | 0.25 | 0.25 | 0.25 | 0.25 | 0.25 |
| % ethoxylanolin | 0.10 | 0.10 | 0.10 | 0.75 | 0.75 | 0.75 | 5.00 | 5.00 | 5.00 |
| iodine/lanolin ratio | 2.50 | 2.50 | 2.50 | 0.33 | 0.33 | 0.33 | 0.05 | 0.05 | 0.05 |

| Ingredients (% w/w) | Formulations | | | | | | | | |
|---|---|---|---|---|---|---|---|---|---|
| | M | N | O | P | Q | R | S | T | U |
| Stock soln reference | A1 | A2 | A3 | B1 | B2 | B3 | C1 | C2 | C3 |
| Stock soln | 96.4 | 96.4 | 96.4 | 96.4 | 96.4 | 96.4 | 96.4 | 96.4 | 96.4 |
| Glycerin-iodine complex | 1.8 | 1.8 | 1.8 | 1.8 | 1.8 | 1.8 | 1.8 | 1.8 | 1.8 |
| DI Water | 1.8 | 1.8 | 1.8 | 1.8 | 1.8 | 1.8 | 1.8 | 1.8 | 1.8 |
| Laneto 50 (from stock) | 0.2 | 0.2 | 0.2 | 1.5 | 1.5 | 1.5 | 10.0 | 10.0 | 10.0 |
| Glycerin (from stock) | 0.0 | 25.0 | 50.0 | 0.0 | 25.0 | 50.0 | 0.0 | 25.0 | 50.0 |
| Amount of undissolved iodine* | 1 | 0 | 0 | 1 | 0 | 0 | 3 | 2 | 0 |
| % avail iodine | 0.5 | 0.5 | 0.5 | 0.5 | 0.5 | 0.5 | 0.5 | 0.5 | 0.5 |
| % ethoxylanolin | 0.10 | 0.10 | 0.10 | 0.75 | 0.75 | 0.75 | 5.00 | 5.00 | 5.00 |
| iodine/lanolin ratio | 5.00 | 5.00 | 5.00 | 0.67 | 0.67 | 0.67 | 0.10 | 0.10 | 0.10 |

| Ingredients (% w/w) | Formulations | | | | | | | | |
|---|---|---|---|---|---|---|---|---|---|
| | V | W | X | Y | Z | AA | BB | CC | DD |
| Stock soln reference | A1 | A2 | A3 | B1 | B2 | B3 | C1 | C2 | C3 |
| Stock soln | 96.4 | 96.4 | 96.4 | 96.4 | 96.4 | 96.4 | 96.4 | 96.4 | 96.4 |
| Glycerin-iodine complex | 3.6 | 3.6 | 3.6 | 3.6 | 3.6 | 3.6 | 3.6 | 3.6 | 3.6 |
| Laneto 50 (from stock) | 0.2 | 0.2 | 0.2 | 1.5 | 1.5 | 1.5 | 10.0 | 10.0 | 10.0 |
| Glycerin (from stock) | 0.0 | 25.0 | 50.0 | 0.0 | 25.0 | 50.0 | 0.0 | 25.0 | 50.0 |
| Amount of undissolved iodine* | 1 | 1 | 0 | 1 | 1 | 0 | 3 | 2 | 0 |
| % avail iodine | 1 | 1 | 1 | 1 | 1 | 1 | 1 | 1 | 1 |
| % ethoxylanolin | 0.10 | 0.10 | 0.10 | 0.75 | 0.75 | 0.75 | 5.00 | 5.00 | 5.00 |
| iodine/lanolin ratio | 10.00 | 10.00 | 10.00 | 1.33 | 1.33 | 1.33 | 0.20 | 0.20 | 0.20 |

*Amount of undissolved Iodine: 0 = none; 1 = trace; 2 = moderate; 3 = major amount In these examples, it was desired to identify minimum and maximum iodine/lanolin ratios with 0.20% xanthan gum added. All formulations from Table 6b had an emulsion-like appearance. Iodine/lanolin ratios of 1:3 to 3:1 were functional (no undissolved iodine) in the absence of glycerin. The functional range of iodine/lanolin ratios expanded as glycerin was added. The workable range of glycerin decreased as iodine level increased.

TABLE 7

Effect of Iodine Solubility in Presence of Sorbitol or Propylene Glycol

| Ingredients (% w/w) | Formulations+ A | B | C | D |
|---|---|---|---|---|
| Stock* | 25.0 | 25.0 | 25.0 | 25.0 |
| Propylene glycol | 25.0 | 50.0 | 25.0 | 50.0 |
| Glycerin-iodine complex | 0.9 | 0.9 | 3.6 | 3.6 |
| DI Water | 49.1 | 24.1 | 46.4 | 21.4 |
| Amount of undissolved iodine^ | 0 | 0 | 2 | 3 |
| iodine/lanolin ratio | 0.33 | 0.33 | 1.33 | 1.33 |
| **Ingredients (% w/w)** | **E** | **F** | **G** | **H** |
| Stock* | 25.0 | 25.0 | 25.0 | 25.0 |
| Sorbitol 70% | 35.7 | 71.4 | 35.7 | 71.4 |
| Glycerin-iodine complex | 0.9 | 0.9 | 3.6 | 3.6 |
| DI Water | 38.4 | 2.7 | 35.7 | 0.0 |
| Amount of undissolved iodine^ | 0 | 0 | 2 | 2 |
| iodine/lanolin ratio | 0.33 | 0.33 | 1.33 | 1.33 |

*Stock solution contains (% w/w) 0.8 xanthan gum; 6.00 Laneto 50; and 93.2 DI water +
Final formulations contain 0.2% xanthan gum and 0.75% lanolin (active)
^Amount of undissolved iodine: 0 = none; 1 = trace; 2 = moderate; 3 = major amount All formulations in Table 7 had an emulsion-like appearance. Propylene glycol and sorbitol produced functional solutions (no undissolved iodine) with an iodine/lanolin ratio of 1:3 but did not produce functional solutions with an iodine/lanolin ratio of 1.33:1.

Table 8a and 8b

TABLE 8a

Legend of Thickeners Used in Table 8b Formulations

| Formulation | Thickener | Type |
|---|---|---|
| D | TIC Ticalose CMC6000 | Carboxymethylcellulose (medium polymerization) |
| E | TIC Ticalose CMC15000 | Carboxymethylcellulose (high polymerization) |
| G | TIC Colloid PM-9399 | Carageenan + NaCl |

TABLE 8b

Formulations Containing Various Thickeners

| Ingredients (% w/w) | Formulations D | E | G |
|---|---|---|---|
| Glycerin | 24.50 | 24.50 | 24.50 |
| Ethoxylanolin 50% | 1.50 | 1.50 | 1.50 |
| Citric Acid monohydrate | 0.10 | 0.10 | 0.10 |
| Thickener D | 0.50 | — | — |
| Thickener E | — | 0.50 | — |
| Thickener G | — | — | 1.00 |
| Glycerin-iodine complex | 0.90 | 0.90 | 0.90 |
| Sodium iodate | 0.10 | 0.10 | 0.10 |
| Aerosol OT 75 | 0.05 | 0.05 | 0.05 |
| NaOH 10% | 0.50 | 0.50 | 0.50 |
| DI Water | 71.85 | 71.85 | 71.35 |
| Appearance | hazy, dark | hazy, dark | hazy, light |
| LV Viscosity, sp 1 | | | |
| 30 rpm | — | — | 138 |
| 12 rpm | 335 | — | 198 |
| 6 rpm | 358 | 716 | 270 |

TABLE 8b-continued

Formulations Containing Various Thickeners

| Ingredients (% w/w) | Formulations D | E | G |
|---|---|---|---|
| LV Viscosity, sp 2 | | | |
| 60 rpm | 300 | >500 | 222 |
| 30 rpm | 346 | 775 | 296 |
| 12 rpm | 402 | 1040 | 465 |
| 6 rpm | <500 | 1260 | 670 |
| Physical stability | | | |
| TOM | ppt | OK | OK |
| 3 weeks | ppt | OK | OK |

Samples E and G were slightly "lumpy" but had no precipitate. It was presumed that the lumps were undissolved thickener.

TABLE 9

Additional Glycerin/Ethoxylanolin Formulations and Characterization

| Ingredients (% w/w) | Formulations A | B | C |
|---|---|---|---|
| Glycerin | 24.50 | 24.50 | 24.50 |
| Ethoxylanolin 50% | 0.20 | 1.00 | 2.00 |
| Citric Acid monohyd | 0.10 | 0.10 | 0.10 |
| Keltrol RD | 0.50 | 0.50 | 0.50 |
| Glycerin-iodine complex | 0.90 | 0.90 | 0.90 |
| Sodium iodate | 0.10 | 0.10 | 0.10 |
| Aerosol OT 75 | 0.05 | 0.05 | 0.05 |
| NaOH 10% | 0.50 | 0.50 | 0.50 |
| DI Water | 73.15 | 72.35 | 71.35 |
| Appearance | hz, dark | hz, less dark | hz, light |

The formulations of Table 9 were prepared and further illustrate the milky or hazy appearance that manifests over certain iodine/ethoxylanolin ratios. All samples achieved a hazy appearance. Formulation C was further evaluated to determine the size of the suspended particles which were believed to be responsible for the formulation's hazy appearance. A Nikon light microscope at 400× magnification was used. A sample of Formulation C was spread undiluted onto a microscope slide. Average particle size was determined to be less than 1000 nm. These results were also confirmed by dynamic light scattering (DLS) testing performed on a Zetasizer instrument. The DLS testing occurred at 25° C. over an 80 second duration. The count rate was 140.3 kcps, the measurement position was 0.65 mm, and the attenuator setting was 3. The DLS testing showed an average particle diameter of 496.9 nm, with the majority of the particles being between 100 to 1000 nm in size.

TABLE 10

| Formulations Containing Xanthan Gum, Buffer, and a Wetting Agent | | | | | | | | | | | | |
|---|---|---|---|---|---|---|---|---|---|---|---|---|
| | Formulations | | | | | | | | | | | |
| | A | B | C | D | E | F | G | H | I | J | K | L |
| Ingredients (% w/w) | | | | | | | | | | | | |
| Glycerin | 24.5 | 24.5 | 24.5 | 24.5 | 24.5 | 24.5 | 24.5 | 24.5 | 24.5 | 24.5 | 24.5 | 24.5 |
| Ethoxylanolin 50% | 1.50 | 1.50 | 1.50 | 1.50 | 1.50 | 1.50 | 1.50 | 1.50 | 1.50 | 1.50 | 1.50 | 1.50 |
| Citric Acid monohydrate | 0.10 | 0.10 | | | 0.10 | 0.10 | | | 0.10 | 0.10 | | |
| Xanthan Gum (Keltrol) | 0.10 | 0.10 | 0.10 | 0.10 | 0.20 | 0.20 | 0.20 | 0.20 | 0.30 | 0.30 | 0.30 | 0.30 |
| Glycerin-iodine complex | 0.90 | 0.90 | 0.90 | 0.90 | 0.90 | 0.90 | 0.90 | 0.90 | 0.90 | 0.90 | 0.90 | 0.90 |
| Aerosol OT 75 | 0.05 | | 0.05 | | 0.05 | | 0.05 | | 0.05 | | 0.05 | |
| NaOH 10% | 0.50 | 0.50 | | | 0.50 | 0.50 | | | 0.50 | 0.50 | | |
| DI Water | 72.35 | 72.4 | 72.95 | 73.0 | 72.25 | 72.3 | 72.85 | 72.9 | 72.15 | 72.2 | 72.75 | 72.8 |
| pH target 5 | x | x | | | x | x | | | x | x | | |
| LV Viscosity, sp2 | | | | | | | | | | | | |
| 60 rpm | 50 | | | | 144 | | | | 268 | | | |
| 30 rpm | 72 | | | | 226 | | | | 445 | | | |
| 12 rpm | 115 | | | | 420 | | | | 880 | | | |
| 6 rpm | | | | | 665 | | | | 1480 | | | |
| TOM | ppt | ppt | ppt | ppt | OK | OK | OK | OK | OK | OK | OK | OK |
| 2.5 weeks | ppt | ppt | ppt | ppt | OK | OK | ppt | slight ppt | OK | OK | OK | OK |

All formulations of Table 10 containing 0.1% xanthan gum had a precipitate. The formulations of Table 10 containing 0.2% xanthan gum had a precipitate in the absence of a buffer, whereas the Aerosol OT75 (wetting agent) appeared to have no effect on these formulations. All formulations of Table 10 containing 0.3% xanthan gum did not have a precipitate and there was no effect by including or omitting a buffer or wetting agent.

TABLE 11

| Effect of High Iodine/Lanolin Ratios on Stability | | | | | | | | | | | | |
|---|---|---|---|---|---|---|---|---|---|---|---|---|
| | Formulations | | | | | | | | | | | |
| Ingredients (% w/w) | A | B | C | D | E | F | G | H | I | J | K | L |
| Glycerin | 0.00 | 0.00 | 0.00 | 0.00 | 0.00 | 0.00 | 50.00 | 50.00 | 50.0 | 50.00 | 50.0 | 50.0 |
| Ethoxylanolin 50% | 0.01 | 0.05 | 0.10 | 0.01 | 0.05 | 0.10 | 0.01 | 0.05 | 0.10 | 0.01 | 0.05 | 0.1 |
| Citric Acid monohydrate | 0.10 | 0.10 | 0.10 | 0.10 | 0.10 | 0.10 | 0.10 | 0.10 | 0.10 | 0.10 | 0.10 | 0.10 |
| Xanthan Gum (Keltrol) | 0.20 | 0.20 | 0.20 | 0.20 | 0.20 | 0.20 | 0.20 | 0.20 | 0.20 | 0.20 | 0.20 | 0.20 |
| Glycerin-iodine complex | 0.90 | 0.90 | 0.90 | 3.60 | 3.60 | 3.60 | 0.90 | 0.90 | 0.90 | 3.60 | 3.60 | 3.60 |
| NaOH 10% to pH 5 | 0.50 | 0.50 | 0.50 | 0.50 | 0.50 | 0.50 | 0.50 | 0.50 | 0.50 | 0.50 | 0.50 | 0.50 |
| DI Water | 98.29 | 98.25 | 98.2 | 95.59 | 95.55 | 95.5 | 48.29 | 48.25 | 48.2 | 45.59 | 45.55 | 45.5 |
| Iodine/lanolin ratio | 51 | 10 | 5 | 205 | 41 | 21 | 51 | 10 | 5 | 205 | 41 | 21 |
| Appearance | clear | hz | hz | slt hz | hz | hz | clear | slt hz | slt hz | clear | slt hz | slt hz |
| Relative free Iodine (on Parafilm) | hi | hi | hi | hi | hi | hi | Lo | lo | lo | hi | hi | hi |
| 1 day ppt | no | no | no | yes | yes | yes | No | no | no | no | no | no |
| 18 days ppt | yes | yes | yes | yes | yes | yes | No | no | no | no | slt ppt | No |
| 6 months ppt | | | | | | | No | No | No | No | No* | No |

*the earlier ppt apparently redissolved

The formulations listed in Table 11 with no added glycerin exhibited a precipitate after 18 days. The 50% glycerin formulations of Table 11 were stable (lack of precipitate) over the testing period.

TABLE 12

Effect of Stability with Varying Ranges of Xanthan Gum

| Ingredients (% w/w) | Formulations A | B | C | D | E | F | G | H | I | J |
|---|---|---|---|---|---|---|---|---|---|---|
| Glycerin | 25.00 | 25.00 | 25.00 | 25.00 | 25.00 | 25.00 | 25.00 | 25.00 | 25.00 | 25.00 |
| Ethoxylanolin 50% | 1.50 | 1.50 | 1.50 | 1.50 | 1.50 | 1.50 | 1.50 | 1.50 | 1.50 | 1.50 |
| Citric Acid monohydrate | 0.10 | 0.10 | 0.10 | 0.10 | 0.10 | 0.10 | 0.10 | 0.10 | 0.10 | 0.10 |
| Xanthan Gum (Keltrol) | 0.16 | 0.18 | 0.20 | 0.22 | 0.24 | 0.16 | 0.18 | 0.20 | 0.22 | 0.24 |
| Glycerin-iodine complex | 0.90 | 0.90 | 0.90 | 0.90 | 0.90 | 3.60 | 3.60 | 3.60 | 3.60 | 3.60 |
| NaOH 10% to pH 5 | 0.50 | 0.50 | 0.50 | 0.50 | 0.50 | 0.50 | 0.50 | 0.50 | 0.50 | 0.50 |
| DI Water | 71.84 | 71.82 | 71.80 | 71.78 | 71.76 | 69.14 | 69.12 | 69.10 | 69.08 | 69.06 |
| Iodine/lanolin ratio | 0.34 | 0.34 | 0.34 | 0.34 | 0.34 | 1.37 | 1.37 | 1.37 | 1.37 | 1.37 |
| 3 days ppt | no | No | no | no | no | yes | yes | no | no | no |
| 10 days ppt | very slight | No | no | no | no | yes | yes | yes | slight | no |

The formulations of Table 12 show that, at an iodine/lanolin ratio of 0.34, the minimum xanthan gum level is between 0.16 and 0.18%. The formulations of Table 12 also show that, at an iodine/lanolin ratio of 1.37, the minimum xanthan gum level is between 0.22 and 0.24%.

TABLE 13

Stability in Presence of Gum Arabic

| | Formulations A | B | C | D | E |
|---|---|---|---|---|---|
| Ingredients (% w/w) | | | | | |
| Glycerin | 25.00 | 25.00 | 25.00 | 25.00 | 25.00 |
| Ethoxylanolin 50% | 1.50 | 1.50 | 1.50 | 1.50 | 1.50 |
| Citric Acid monohydrate | 0.10 | 0.10 | 0.10 | 0.10 | 0.10 |
| 5% gum arabic | 70.00 | 40.00 | 10.00 | 6.00 | 3.00 |
| Glycerin-iodine complex | 0.90 | 0.90 | 0.90 | 0.90 | 0.90 |
| NaOH 10% to pH 5 | 0.50 | 0.50 | 0.50 | 0.50 | 0.50 |
| DI Water | 2.00 | 32.00 | 62.00 | 66.00 | 69.00 |
| % gum arabic | 3.5 | 2 | 0.5 | 0.3 | 0.15 |
| LV Viscosity, UL adapter | | | | | |
| 60 rpm | 4.4 | 3.2 | 2.3 | | |
| initial ppt | | | | OK | ppt |
| 1 day ppt | slt ppt | no | no | | |
| 6 days ppt | mod ppt | mod ppt | slt ppt | slt residue | mod ppt |

The formulations of Table 13 show that, at 6 days after preparation, all gum arabic containing formulations had some precipitate. Further, the formulations of Table 13 suggest that less gum arabic may perform better (less precipitate).

TABLE 14

Gum Arabic and Xanthan Gum Containing Formulations with Low Iodine

| Ingredients (% w/w) | Formulations A | B | D | E | F* | G* | H | I |
|---|---|---|---|---|---|---|---|---|
| Glycerin | 25.00 | 25.00 | 25.00 | 25.00 | 25.00 | 25.00 | | |
| Ethoxylanolin 50% | 1.50 | 1.50 | 1.50 | 1.50 | 1.50 | 1.50 | 1.50 | 1.50 |
| Citric Acid monohydrate | 0.10 | 0.10 | 0.10 | 0.10 | 0.10 | 0.10 | 0.10 | 0.10 |
| 5% gum arabic | 60.00 | 30.00 | 6.00 | 40.00 | | | | |
| Xanthan gum | | | 0.05 | 0.05 | 0.20 | 0.20 | 0.20 | 0.20 |
| NaI—$I_2$ complex | 1.80 | 1.80 | 0.45 | 0.45 | | | 0.07 | 0.18 |
| Glycerin-iodine complex | | | | | 0.18 | 0.35 | | |
| NaOH 10% to pH 5 | | | | | 0.50 | 0.50 | 0.50 | 0.50 |
| DI Water | 11.60 | 41.60 | 66.90 | 32.90 | 72.52 | 72.35 | 97.63 | 97.52 |
| % avail iodine | 1.03 | 1.03 | 0.26 | 0.26 | 0.05 | 0.10 | 0.04 | 0.10 |
| % gum arabic | 3 | 1.5 | 0.3 | 2 | 0 | 0 | 0 | 0 |
| % xanthan gum | 0.00 | 0.00 | 0.05 | 0.05 | 0.20 | 0.20 | 0.20 | 0.20 |
| Initial | ppt | ppt | OK | OK | OK | OK | ppt | ppt |
| 1 day phys stability | | | Ppt | ppt | | | | |
| 10 days phys stability | | | | | OK | OK | | |

*G was slightly hazier than F

The gum arabic containing formulations of Table 14 all produced a precipitate. Formulations containing xanthan gum as the only thickener did not precipitate with an iodine content as low as 0.05% w/w.

TABLE 15

Additional Gum Arabic and Xanthan Gum Containing Formulations

| | Formulations | | | | | | | |
|---|---|---|---|---|---|---|---|---|
| | J | K | L | M | N | O | P | Q |
| Ingredients (% w/w) | | | | | | | | |
| Glycerin | 0 | 0 | 50.00 | 50.00 | 25.00 | 25.00 | 0 | 0 |
| Ethoxylanolin 50% | 1.50 | 1.50 | 1.50 | 1.50 | 1.50 | 1.50 | 1.50 | 1.50 |
| Citric Acid monohydrate | 0.10 | 0.10 | 0.10 | 0.10 | 0.10 | 0.10 | 0.10 | 0.10 |
| 5% gum arabic | 0 | 0 | 0 | 0 | 5.00 | 10.00 | 5.00 | 10.00 |
| Xanthan gum | 0.50 | 0.50 | 0.20 | 0.20 | 0.10 | 0.10 | 2.00 | 2.00 |
| NaI—$I_2$ complex | 0.10 | 0.22 | 0.10 | 0.22 | 0.18 | 0.17 | 0.24 | 0.18 |
| NaOH 10% to pH 5 | 0.50 | 0.50 | 0.50 | 0.50 | 0.50 | 0.50 | 0.50 | 0.50 |
| DI Water | 97.30 | 97.18 | 47.60 | 47.48 | 67.62 | 62.63 | 90.66 | 85.72 |
| % avail iodine | 0.06 | 0.13 | 0.06 | 0.13 | 0.10 | 0.10 | 0.14 | 0.10 |
| % gum arabic | 0 | 0 | 0 | 0 | 0.25 | 0.5 | 0.25 | 0.5 |
| % xanthan gum | 0.50 | 0.50 | 0.20 | 0.20 | 0.10 | 0.10 | 2.00 | 2.00 |
| Physical stability | | | | | | | | |
| initial | Ok | OK | OK | OK | OK | OK | OK | OK |
| 1 day | OK | OK | OK | OK | OK | OK | ppt | ppt |
| 1 wk | OK | OK | OK | OK | OK | OK | | |
| 2 month | OK | OK | OK | OK | ppt | ppt | | |

All formulations from Table 15 containing both gum arabic and xantham gum produced a precipitate while formulations containing only xanthan gum did not form a precipitate even after two months.

Table 16, below, summarizes certain broad, intermediate and narrow ranges for components present in certain embodiments according to the present invention.

TABLE 16

| Ingredients (% w/w) | Broad Range | Intermediate range | Narrow range | Exemplary amount |
|---|---|---|---|---|
| Iodine (germicide) | 0.05-1.5 | 0.15-0.9 | 0.20-0.75 | 0.25 |
| Primary emollient (e.g., glycerine) | 0-75 | 10-50 | 20-30 | 25.00 |
| Secondary emollient (e.g., ethoxylated lanolin) | 0.01-10 | 0.1-5 | 0.5-3 | 0.75 |
| Iodide ion (e.g., sodium iodide) | 0-1 | 0.001-0.5 | 0.01-0.25 | 0.11 |
| Iodate ion (e.g., sodium iodate) | 0-1 | 0.001-0.5 | 0.01-0.25 | 0.10 |
| Wetting agent (e.g., sodium dioctylsulfo-succinate) | 0-2 | 0.001-0.25 | 0.005-0.1 | 0.04 |
| Thickener (e.g., xanthan gum) | 0-5 | 0.01-2 | 0.05-1 | 0.50 |
| Buffer/pH adjuster (e.g, citric acid, sodium hydroxide) | 0-2 | 0.01-1 | 0.05-0.5 | 0.14 |
| Water | 10-99 | 30-85 | 60-80 | 73.11 |

I claim:

1. A ready-to-use germicidal composition comprising:

from about 25 to about 50% by weight of a primary emollient selected from the group consisting of glycerin, propylene glycol, sorbitol, polyethylene glycol, and mixtures thereof;

from about 0.05 to about 10% by weight of a water-soluble lanolin derivative; and from about 0.05 to about 1.5% by weight of iodine, wherein the weight ratio of iodine to said water-soluble lanolin derivative is from about 0.3 to about 10;

said composition comprising less than 1% by weight of iodine complexing surfactants and iodine complexing polymers, wherein the weight ratio of iodine to total iodine complexing surfactants and iodine complexing polymers is greater than 0.5, said composition being ready to apply to an animal's teat without further dilution.

2. The germicidal composition according to claim 1, wherein said composition further comprises a thickener.

3. The germicidal composition according to claim 2, wherein said thickener comprises up to 5% by weight of said composition and is selected from the group consisting of hydroxy ethylcellulose and carboxy methylcellulose, sodium alginate, xanthan gum, gum arabic, and mixtures thereof.

4. The germicidal composition according to claim 1, wherein said water-soluble lanolin derivative comprises an alkoxylated lanolin.

5. The germicidal composition according to claim 4, wherein said alkoxylated lanolin comprises ethoxylated lanolin.

6. The germicidal composition according to claim 1, wherein said primary emollient comprises glycerin.

7. The germicidal composition according to claim 1, wherein said composition has a viscosity of between about 2 to about 5000 cP.

8. The germicidal composition according to claim 1, wherein said composition comprises particles suspended therein, said suspended particles having an average diameter of between about 25 nm to about 5 μm.

9. A ready-to-use germicidal composition comprising:

from about 25 to about 50% by weight of a primary emollient selected from the group consisting of glycerin, propylene glycol, sorbitol, polyethylene glycol, and mixtures thereof;

a secondary emollient selected from the group consisting of water-soluble lanolin derivatives, said secondary emollient being present in an amount less than said primary emollient, wherein the weight ratio of iodine to said secondary emollient is from about 0.05 to about 41, wherein the weight ratio of said primary emollient to said secondary emollient is greater than 5;

at least about 0.2% by weight of at least one thickener; and from about 0.05 to about 1.5% by weight of iodine, said composition comprising less than 1% by weight of iodine complexing surfactants and iodine complexing polymers, wherein the weight ratio of iodine to total iodine complexing surfactants and iodine complexing polymers is greater than 0.5, said composition being storage stable for at least one month and ready to apply to an animal's teat without further dilution.

10. The germicidal composition according to claim 9, wherein said thickener comprises up to 5% by weight of said composition and is selected from the group consisting of hydroxy ethylcellulose and carboxy methylcellulose, sodium alginate, xanthan gum, gum arabic, and mixtures thereof.

11. The germicidal composition according to claim 9, wherein said water-soluble lanolin derivative comprises an alkoxylated lanolin.

12. The germicidal composition according to claim 11, wherein said alkoxylated lanolin comprises ethoxylated lanolin.

13. The germicidal composition according to claim 9, wherein said primary emollient comprises glycerin.

14. The germicidal composition according to claim 9, wherein said composition comprises particles suspended therein, said suspended particles having an average diameter of between about 25 nm to about 5 μm.

15. A ready-to-use germicidal composition comprising:

from about 0.05 to about 1.5% by weight of iodine, from 0.05 to about 10% by weight of water-soluble lanolin derivative, wherein the weight ratio of iodine to said water-soluble lanolin derivative is from about 0.3 to about 3, wherein said composition comprises less than 0.5% by weight of iodine complexing surfactants and iodine complexing polymers, wherein the weight ratio of iodine to total iodine complexing surfactants and iodine complexing polymers is greater than 0.5; and at least about 0.2% by weight of at least one gum thickener, said composition being storage stable for at least one month and ready to apply to an animal's teat without further dilution.

16. The germicidal composition according to claim 15, wherein said at least one gum thickener comprises a mixture of at least two gums.

17. The germicidal composition according to claim 16, wherein said at least one gum thickener comprises gum arabic and xanthan gum.

18. The germicidal composition according to claim 17, wherein said at least one gum thickener comprises from about 0.1 to 5% by weight of gum arabic and from about 0.05 to 0.5% by weight of xanthan gum.

19. The germicidal composition according to claim 15, wherein said water-soluble lanolin derivative comprises an alkoxylated lanolin.

20. The germicidal composition according to claim 19, wherein said alkoxylated lanolin comprises ethoxylated lanolin.

21. The germicidal composition according to claim 15, wherein said composition exhibits a viscosity of between about 30 to about 5000 Cps.

22. The germicidal composition according to claim 15, wherein said composition comprises particles suspended therein, said suspended particles having an average diameter of between about 25 nm to about 5 μm.

23. A method of protecting a bovine teat from infection comprising applying to said bovine teat a quantity of a composition according to claim 9.

* * * * *